(12) United States Patent
Thro et al.

(10) Patent No.: US 7,937,240 B2
(45) Date of Patent: May 3, 2011

(54) METHOD AND DEVICE FOR CHARACTERIZING, USING ACTIVE PYROMETRY, A THIN-LAYER MATERIAL ARRANGED ON A SUBSTRATE

(75) Inventors: Pierre-Yves Thro, Gif-sur-Yvette (FR); Francois Brygo, Orsay (FR); Sergey Fomichev, Paliseau (FR); Alexandre Semerok, Paliseau (FR)

(73) Assignee: Commissariat a l'Energie Atomique et Aux Energies Alternatives, Paris (FR)

( * ) Notice: Subject to any disclaimer, the term of this patent is extended or adjusted under 35 U.S.C. 154(b) by 320 days.

(21) Appl. No.: 12/224,064

(22) PCT Filed: Feb. 15, 2007

(86) PCT No.: PCT/FR2007/050803
§ 371 (c)(1),
(2), (4) Date: Oct. 21, 2008

(87) PCT Pub. No.: WO2007/093744
PCT Pub. Date: Aug. 23, 2007

(65) Prior Publication Data
US 2010/0100352 A1    Apr. 22, 2010

(51) Int. Cl.
*G01K 11/30* (2006.01)
(52) U.S. Cl. .................................................. 702/136

(58) Field of Classification Search ........... 702/134–136
See application file for complete search history.

(56) References Cited

U.S. PATENT DOCUMENTS
5,957,581 A    9/1999    Katzir et al.
2002/0031164 A1    3/2002    Scheidt et al.

FOREIGN PATENT DOCUMENTS
DE     19520788    7/1996
FR      2647547    11/1990
WO    WO-01/44752    6/2001

*Primary Examiner* — Drew A Dunn
*Assistant Examiner* — Stephen J Cherry
(74) *Attorney, Agent, or Firm* — IM IP Law PLLC; C. Andrew Im

(57) ABSTRACT

The present invention relates to a method for characterizing a material using active pyrometry. The material comprises at least one thin surface layer arranged on a thick substrate. The present invention heats the surface ($Z_{TH}$) of the material by exposing the material to high-frequency laser pulses, so as to perform a series of temperature increase/decrease thermal cycles, accompanied by a heat build-up from one cycle to the next. The present invention collects the emitted radiation, acquires and processes the signals measured by comparing the measured values to the theoretical values obtained by modelling, so as to obtain thermo-physical properties for characterizing the material. The present invention also relates to a device for implementing the method comprising a high-frequency pulsed laser used as heat source.

19 Claims, 2 Drawing Sheets

FIG_1
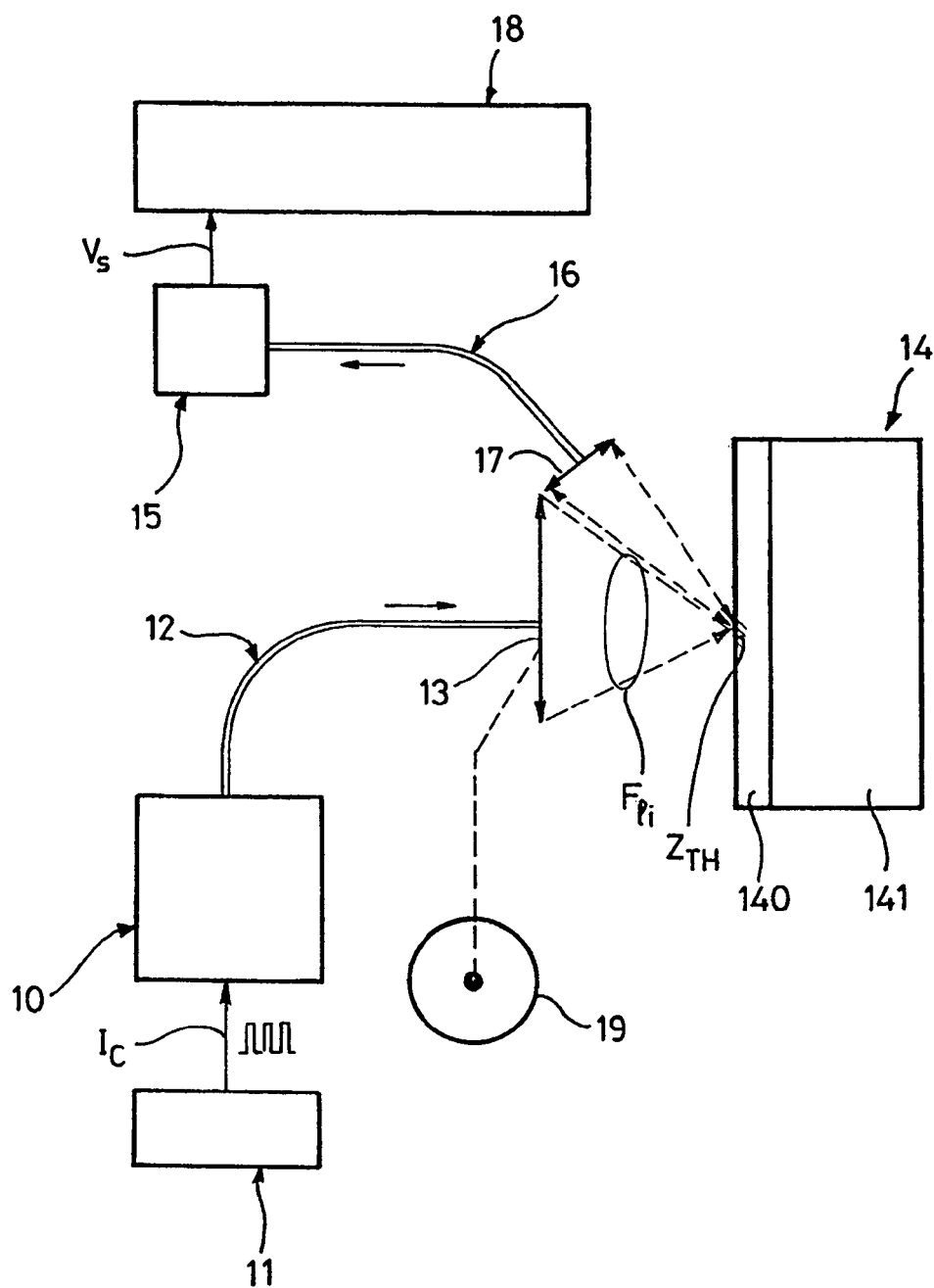

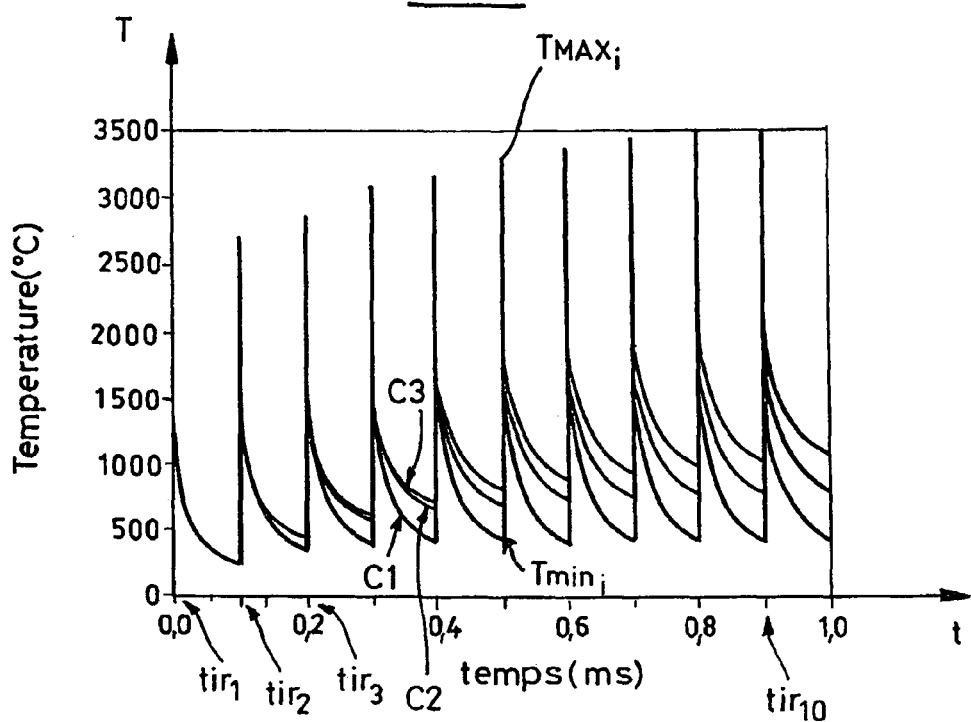
FIG_2
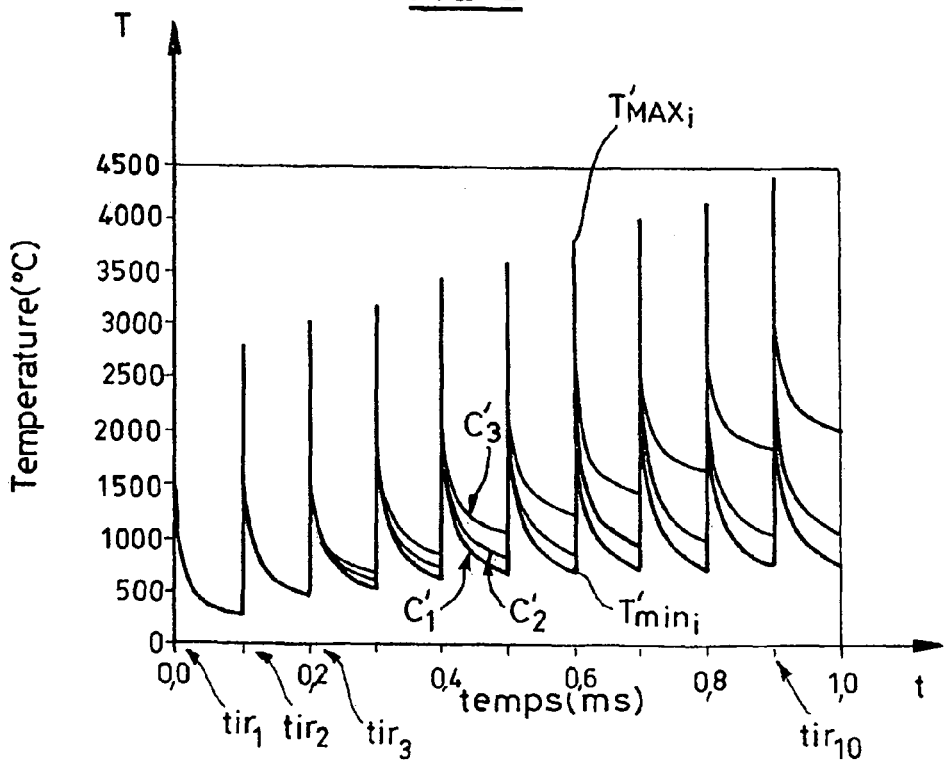
FIG_3

METHOD AND DEVICE FOR CHARACTERIZING, USING ACTIVE PYROMETRY, A THIN-LAYER MATERIAL ARRANGED ON A SUBSTRATE

RELATED APPLICATIONS

This application claims priority from PCT/FR2007/050803 filed Feb. 15, 2007, which claims priority from French Application No. 06 01471 filed Feb. 17, 2006, each of which is herein incorporated by reference in its entirety.

TECHNICAL FIELD

The present invention concerns a method for characterizing a block of material comprising at least one thin layer disposed on a thicker substrate.

The invention also concerns a device for implementing the method.

In the context of the invention, "characterizing" is understood to mean analyzing predetermined physical properties of a thin-layer material by measuring the thermal emission from the surface of this material, which is heated by means of a laser heating system.

Likewise, in the context of the invention, it should be understood that the thin layer of material can be composed of a single layer (monolayer) or of several superposed layers (multilayer).

The invention is applicable to various fields. To give a non-exhaustive list, these include the characterization of physical properties of material deposits, thin layers, and oxide layers, and the characterization of impurities present on the surfaces of materials.

BACKGROUND OF THE INVENTION

As is well known, any material will emit electromagnetic radiation, whose intensity as a function of wavelength depends on its temperature. This intensity is described by Planck's law.

Methods for measuring the electromagnetic radiation emitted by the material and for deducing its temperature have been developed for a long time. These methods may be qualified as "passive" measurement methods, since they measure only the temperature of the material, from which the predetermined physical properties are deduced.

These methods have the advantage of being non-intrusive, since they do not require physical contact between a measuring device and the material.

On the other hand, there are other proposed temperature measuring methods which do require contact between a measuring device and the material. These include, for example, the use of thermocouples. This type of measurement has other drawbacks. In particular, the measurement cannot be performed without advance preparation of the block of material.

Improved methods of the aforementioned "contactless" type have also been proposed in the Prior Art, including a method of measurement using so-called "active" pyrometry. A method of this type consists of heating the block of material using a heat source, for example a laser, and of measuring the radiation from the body that results from the heating in order to deduce its temperature. The radiation is analyzed using an electromagnetic radiation collecting device, a sensor that converts the electromagnetic energy into electrical signals and an electronic signal processing system. Analyzing the temperature and its time evolution makes it possible to deduce certain physical properties of the material, for example its thermal conductivity, its absorptivity, or in the case of a multilayer material sample, the thickness of the layers and the thermal resistance between two layers.

Methods of this type for analyzing the physical properties of materials by measuring the temperature using active pyrometry have been known for many years.

They include, to give a non-exhaustive list of examples, the following methods:

French patent application FR 2 593 917 A1 (UNIVERSITY OF REIMS-CHAMPAGHE-ARDENNE) describes a method for measuring the absorptivity, the diffusivity and the thermal resistance between two layers of material. The material sample is composed of a thin layer, which is transparent to the wavelength of the electromagnetic radiation, disposed on a thick substrate. The substrate is heated using a laser beam that is amplitude-modulated at a high frequency and a low frequency. The thermal emission from the substrate is then measured. Analyzing the phase difference between the thermal emission and the laser signal makes it possible to determine the physical properties of the transparent thin layer.

French patent application FR 2 647 547 A1 (UNIVERSITY OF REIMS-CHAMPAGHE-ARDENNE) describes a method for measuring the thermal contact resistance between two layers that are opaque to laser radiation. The surface of the material sample is heated using a modulated laser beam, and analyzing the modulated component of the surface temperature makes it possible to determine the value of the thermal contact between the two layers. However, this method requires that a prior calibration be performed on a set of representative test samples of the material to be analyzed.

French patent application FR 2 663 745 A1 (UNIVERSITY OF REIMS-CHAMPAGHE-ARDENNE) describes a method similar to that of the preceding patent application. However, the modulation of the laser beam is obtained using a pseudo-random binary signal.

The above-mentioned methods use modulated laser beams. Other methods are described in the literature as applying a pulsed heating signal, i.e., using for example a laser that emits short (a few nanoseconds), high-intensity pulses. These features offer several advantages. First, the resulting temperature increase is higher, thus making it possible to also obtain a higher electromagnetic radiation of the surface, and hence a better precision in the measurement, by increasing the signal-to-noise ratio.

Finally, another method of active pyrometry in the Prior Art proposes using a laser beam that is modulated and pulsed. Such a method was described, for example, by T. Loarer in the doctoral thesis entitled: Mesure de □odule□ture de surface par effet photothermique □odule ou impulsionnel ["Surface temperature measurement by means of a modulated or pulsed photothermal effect"], Ecole Centrale Paris, (1989).

This method was the subject of an Israeli patent application, filed under the number IL 1996118611, which corresponds to U.S. Pat. No. 5,957,581 (Katzir et al.).

These documents describe a method for measuring surface temperature by analyzing the temporal shape of the decrease in temperature after a laser shot, without taking into account the value of the maximum temperature. This method has the particular advantage of making it possible to dispense with the in situ calibration of the measuring device.

The above-mentioned methods of the Prior Art admittedly have advantages, but they do not entirely meet current needs in the fields of application for which the invention is intended. Moreover, while the last method described would, in theory, seem to be the most advantageous, it should noted that it is not easy to use for analyzing layers of material having thicknesses on the order of a few micrometers. In fact, when the material is heated using a pulsed laser, only a small thickness of material near the surface is actually heated, and the influence of the thickness of the thin superficial layer and of the thermal contact between this superficial layer and a substrate are not easy to establish. Finally, modulated laser beam heating, while admittedly making it possible to measure the physical properties of multilayer material samples, is a method that suffers from a low "signal-to-noise" ratio.

SUMMARY AND OBJECT OF THE INVENTION

The object of the invention is to overcome the drawbacks of the methods of the Prior Art, some of which have been mentioned, and also to meet current needs in the field.

In essence, the invention makes it possible both to obtain a very good "signal-to-noise" ratio, thus making it possible to obtain predetermined information on the single superficial layer alone, such as its thermal diffusivity and density, and to heat the material to a sufficient depth for the entire thickness of the thin superficial layer, and/or the thermal contact between the two layers, to actually be involved.

To this end, according to an important feature, the invention uses a laser pulsed at a high firing rate to heat the surface of a block of multilayer material. This block of material includes one or more layer(s) of small thickness, hereinafter called the "superficial layer(s)." The superficial layers, disposed on a thicker layer, hereinafter called the "substrate," are subjected to the pulsed laser radiation and absorb it. In theory, the value of the thermal contact between the substrate and the superficial layers can be any value, even zero.

According to another important feature of the invention, the firing rate, i.e. the pulse repetition frequency, is chosen so as to be high enough to enable an accumulation of heat to be obtained, shot after shot, in the superficial layer of the material. In essence, in that case, the heated material does not have time to cool completely between two successive shots.

According to yet another important feature, the heating of the material during a single shot makes it possible to obtain information on the superficial layer of the material, i.e. in the volume that absorbs the laser radiation.

According to yet another important feature, the accumulation of heat resulting from a salvo of successive shots makes it possible to obtain information on areas located at deeper thicknesses.

According to yet another important feature, the evolution of the radiation from the surface of the material makes it possible to determine the evolution of the temperature, which is analyzed using a numerical model based on the heat equation and on conditions at the limits specific to the material to be analyzed. This can be done using mathematical tools well known to the Person Skilled in the Art.

Thus, the main subject of the invention is a method for characterizing a block of material using active pyrometry, said block of material comprising at least two superposed layers, a superficial layer of small thickness disposed on a thick substrate, said superficial layer being brought to a predetermined initial temperature, characterized in that it includes at least the following steps:

a first step consisting of heating at least one predetermined area of the surface of said superficial layer of material using a salvo of laser pulses, the repetition frequency of said laser pulses being chosen so that it is high enough, and their duration is short enough, for the material of said superficial layer to go through a plurality of thermal cycles consisting of a rapid temperature increase when it is exposed to said laser pulses followed by a slow temperature decrease between two laser pulses in which it is not allowed to return to said initial temperature, and for it to accumulate heat from one thermal cycle to the next;

a second step consisting of collecting all or part of the thermal radiation emitted by the surface of said material;

a third step consisting of measuring at least part of said collected thermal radiation using a sensor;

a fourth step consisting of determining the temperature of said surface from said thermal radiation measured by said sensor and processed by a signal acquisition and processing system; and a fifth step consisting of analyzing predetermined time regimes by comparing the measurements acquired by the signal acquisition and processing system with theoretical values given by the heat equation adapted to the physical characteristics of said material, and of matching up these two series of values by varying at least one physical parameter associated with said material, so as to derive predetermined thermophysical properties of same for said characterizing of the superficial layer.

Another subject of the invention is a device for implementing the method.

BREIF DESCRIPTION OF THE DRAWING

Other features and advantages of the invention will emerge from the following detailed description, with the help of the attached figures, in which:

FIG. 1 schematically illustrates an exemplary embodiment of a device for implementing the method according to the invention;

FIG. 2 represents curves illustrating the temperature evolution of thin layers of materials of different thicknesses subjected to a plurality of successive laser shots at a high rate; and FIG. 3 represents curves illustrating the temperature evolution of thin layers of materials subjected to a plurality of successive laser shots at a high rate, said layers being disposed on a thick substrate and having thermal contacts with this substrate of different values.

DETAILED DESCRIPTION OF THE EMBODIMENTS

FIG. 1 schematically illustrates an exemplary embodiment of a device for implementing the method according to the invention.

The device 1 includes as a heat source a laser 10, for example a diode-pumped "Nd:YAG" (neodymium-doped) laser. Its frequency is doubled using a nonlinear KTP (potassium titanyl phosphate) crystal, not shown in FIG. 1. To clarify, in a practical embodiment, the wavelength is 532 nm, with a typical pulse duration of 90 ns. The laser 10 operates at a high firing rate, preferably at a frequency of 10 kHz, but can be within a typical range of 1 kHz to 30 kHz. To this end, conventional electronic circuits 11 generate control pulses $I_c$, which are transmitted to the laser 10. Advantageously the laser beam is injected into a multimode optical fiber 12, making it possible to homogenize the spatial profile of the optical intensity. Via an output, the optical fiber 12 is coupled with one or more optical lenses, only one of which 13 is shown in FIG. 1. The lens 13 is disposed so as to make it possible to obtain, on the surface of a block of material 14, an incident beam $F_h$ of homogeneous intensity, focused on an area to be heated $Z_{TH}$ whose surface area typically varies between 0.2 and 5 mm$^2$, with a fluency of between 0.01 and 4 J/cm$^{-2}$. The incident laser beam $F_h$ makes it possible to heat the surface of the block of material 14. This block of material 14 whereof predetermined thermophysical properties need to be known is composed of at least two layers: a superficial layer 140, of small thickness, and a substrate 141 of large thickness compared to that of the superficial layer 140. The thickness of the layer 140 is typically within a range of 0.1 μm to 900 μm.

Without going beyond the scope of the invention, the block of material 14 can comprise several superposed superficial layers of small thickness.

The temperature measurement is performed using a sensor that is sensitive in a range of thermal radiation wavelengths, thus making it possible to obtain enough signal, yet this range is different enough from the wavelength emitted by the laser 10 so that the latter does not interfere with the measurement. Moreover, this sensor 15 has response time that is much shorter than the time between two consecutive shots. This sensor 15 converts the thermal radiation into electrical output signals $V_s$ transmitted to a signal acquisition and processing system 18. The signal acquisition and processing system 18 makes it possible to deduce the temperature using methods known to the Person Skilled in the Art. In the embodiment described in FIG. 1, the sensor 15 is coupled with an optical fiber 16, itself coupled via an input to one or more optical lenses, only one of which 17 is shown. The optical lens 17 collects the radiation emitted by the surface of the block 14.

In an additional embodiment (not illustrated), the "sensor 15—signal acquisition and processing system 18" combination can be replaced by a pyrometer. In a practical exemplary embodiment, a Kleiber® C-LWL pyrometer, which is sensitive in a wavelength range of between 1.58 and 2.2 μm, is used. This measuring device is equipped with a lens for collecting part of the radiation emitted by the material under test.

In a preferred embodiment, the signal acquisition and processing system 18 is embodied by means of a computer system with a stored program, comprising specific acquisition cards that receive the signals converted by the sensor 15 and associated with the LabVIEW® ("Laboratory Virtual Instrument Engineering Workbench") software. This type of operating mode is intrinsically well known to the Person Skilled in the Art and there is no need to describe it further.

In a preferred embodiment, the temperature analysis can be performed using specialized software, for example the MATLAB® interactive calculation software available on the market, which makes it possible to perform numerical simulations based on numerical analysis algorithms. In the context of the invention, this software makes it possible to solve the heat equation in the medium under test in question, taking into account an internal heat source representing the laser pulse heating. Thermophysical parameters such as the thickness of the layer, the thermal resistance between the two layers, the thermal diffusivity, the absorption coefficient and/or the density of the material are variables, and can be adjusted based on experimental results.

Creating a calculation program using software of this type is an operation that is intrinsically within the capability of the Person Skilled in the Art. Here again, there is no need to describe it in further detail.

In a preferred embodiment, the heating and the radiation measurement are carried out in a controlled atmosphere, for example in a nitrogen, argon or vacuum atmosphere. In an additional variant of embodiment (not illustrated), a gas jet can be sprayed onto the surface of the material (the superficial layer 140) in order to prevent any influence of the ambient atmosphere on the heated surface.

In another embodiment, in order to obtain a mapping of the thermophysical properties of the superficial layer, the heating of the material can also be obtained using a laser beam scanned over the surface under the control of a galvanometric scanning device, for example comprising a motor 19 mechanically coupled with an array of optical elements 13 (mirrors and lenses) disposed on a rotating shaft. In this embodiment, the optical lens 17 for collecting the thermal radiation must be moved so as to continuously collect the thermal radiation issuing from the area heated by the laser.

In another embodiment, in order to obtain a mapping of the thermophysical properties of the superficial layer, the surface of the material 14 is moved past the array of optical lenses 13.

We will now describe a first example of the results obtained using the method of the invention, in reference to FIG. 2.

It is assumed that the high-frequency pulsed laser beam generated by the laser 10 in FIG. 1 is projected onto a block of material 14 comprising two layers, a superficial layer 140 and a substrate 141. It is also assumed that the superficial layer 140 of small thickness is composed of a material that is highly absorbent of the electromagnetic radiation of the beam generated by the laser 10 and not very thermally diffusive on the surface.

The experiment is repeated for superficial layers 140 of various thicknesses, i.e. 2, 3 and 4 μm in the example described (curves $C_1$ through $C_3$, respectively).

The material is heated by laser pulses of very short duration (90 ns) emitted at a high firing rate (10 kHz). As mentioned above, according to one of the important features of the invention, this choice of frequency makes it possible to accumulate heat, shot after shot, because the superficial material 140 does not have time to cool completely between pulses.

It is assumed in the example in FIG. 2 that the salvo of shots comprises ten successive shots (laser pulses) $tir_1$ through $tir_{10}$, repeated after a time interval of 0.1 ms (the horizontal time axis t, graduated from 0 to 1 ms).

The laser pulses, synchronized with the instants 0 through 0.9 ms on the time axis t of FIG. 2, cause sudden temperature increases, with the successively reached temperatures culminating in values $Tmax_i$ (typically between 3,000 and 3,500° C.: the vertical axis T of temperatures from 0 to 3500° C.) which increase steadily from one shot to the next. When a laser pulse stops, the temperature of the superficial layer of material 140 decreases, but much more slowly than it increased during the temperature increase (natural cooling), so as to reach minimum values $Tmin_i$ (typically between 250 and 500° C.) that increase steadily from one shot to the next.

It is easy to see in FIG. 2 that the evolution of the temperature in a single shot (the first shot, $tir_1$) does not make it possible to distinguish any notable differences in behavior between the various layer thicknesses; the curves $C_1$ through $C_3$ are practically the same. On the other hand, the accumulation of heat, shot after shot, makes it possible to distinguish a clear difference between the various layer thicknesses. In the example described in FIG. 2, this difference between the curves $C_1$ through $C_3$ becomes completely perceptible beginning with the third pulse, $tir_3$.

An additional series of experiments was conducted, this time no longer varying the thickness of the superficial layer 140, but choosing a thin layer of material that was highly conductive and not very diffusive on the surface, disposed on a highly thermally diffusive material forming a thick substrate 141. To conduct these experiments, three different thermal contact values were selected.

The thermal contact values were divided into three classes, with two extremes: "perfect" thermal contacts and "no contact," respectively. An "intermediate" thermal contact value was also chosen. The respective curves $C'_1$, $C'_3$ and $C'_3$ in FIG. 3 correspond to the three aforementioned classes.

As before, the horizontal axis is graduated in time units t (from 0 to 1 ms), the vertical axis in temperature units T (from 0 to 4,500° C.), and the salvo of shots comprises ten pulses, $t_1$ through $t_{10}$, repeating every 0.1 ms and having a duration equal to 90 ns.

The successively reached temperatures culminate in values T'$max_i$ (typically between 2,500 and 4,500° C.) which increase steadily from one shot to the next. In the same way as in the preceding case, when are laser pulsing stops, the temperature decreases, but much more slowly than it increases during the temperature increase, so as to reach minimum values T'$min_i$ (typically between 250 and 750° C.) that also increase steadily from one shot to the next.

Here again, it is not possible to see differences between the thermal contacts of different classes with a single shot (the first pulse $tir_1$). The curves $C'_1$ through $C'_3$ are practically the same. On the other hand, the accumulation of heat, shot after shot, makes it possible to reveal the difference in behavior between the various classes of contacts, here again beginning with the third pulse $tir_3$, in the example described in FIG. 3. Moreover, this differentiation becomes greater and greater, again in the example described, between the "no contact" class (curve $C'_3$) and the other two classes (curves $C'_1$ and $C'_3$).

In the two exemplary experiments described above, it is possible to obtain a set of predetermined information on the superficial layer 140 by analyzing predetermined heating and cooling time regimes of said material (140). The analysis focuses on all or some of the following regimes: the measurement of the average increase in its temperature, the time evolution of the temperature during the heating in each thermal cycle or selectively for predetermined thermal cycles, the average temperature value reached at saturation, the maximum temperature value ($Tmax_i$) reached for each thermal cycle or selectively for predetermined thermal cycles, the temperature value reached just before each laser pulse or selectively before predetermined laser pulses, the temperature value in one or more predefined time intervals between two laser pulses as compared to the previous laser pulse, the-time evolution of the temperature between two laser pulses, the time evolution of the temperature after the end of said salvo of laser pulses and/or the temperature value reached in one or more predetermined periods after said salvo of laser pulses (not illustrated in FIGS. 2 and 3).

The main steps of the method according to the invention will now be described in detail.

A first step consists of heating the surface of a block of material 14 comprising at least two different layers, a superficial layer 140 of small thickness, typically on the order of one micrometer, disposed on a thick (in comparison with the thickness of the superficial layer 140) substrate 141. However, the thickness of the superficial layer 140 can be greater or less than one micrometer without going beyond the scope of the invention. The heating is performed using a laser 10, pulsed at a high firing rate so the material absorbs the laser radiation, heats up and partially cools between two shots. In essence, the firing rate, i.e. the repetition frequency of the pulses delivered by the laser 10, is chosen so as to be high enough so that the maximum temperature $Tmax_i$ reached cannot fall back ($Tmin_i$) to the initial temperature. The number of shots applied to the block of material 14 can be high enough so that the average temperature increase reaches saturation and remains substantially constant, but it can also be lower, depending on the type of measurement to be performed. The energy of the laser pulses must be high enough so that the thermal signal can be measured with a sufficient signal-to-noise ratio. Since the measurement must be nondestructive, it is understood that this energy must also be low enough not to damage the material.

A second step consists of collecting all or part of the thermal radiation emitted by the surface of the material. The collection and transport of the radiation can be performed using optical lenses 17 and an optical fiber 16.

A third step consists of measuring at least part of this collected thermal radiation using a sensor 15 whose spectral sensitivity range is adapted to the radiation emitted by the target and converting it into electrical signals.

The measurement can be performed, for example, using a pyrometer, advantageously a multi-channel pyrometer in order to eliminate the emissivity specific to the material. In that case, the second and third steps can be combined into a single step, since the pyrometer is normally provided with a lens that collects the radiation emitted by the material under test.

A fourth step consists of analyzing predetermined heating time regimes of the material, i.e., in particular, the average increase in the temperature, the time evolution of the temperature during the heating with each shot (i.e., with each laser pulse) or selectively for predetermined shots, the average maximum temperature value, the maximum temperature value $Tmax_i$ reached for each shot or selectively for predetermined shots, the temperature value reached just before each shot, T'$min_i$, or selectively before predetermined shots, the temperature value in one or more time intervals between two shots as compared to the previous shot, the time evolution of the temperature between two shots, the time evolution of the temperature after the salvo of shots, and/or the temperature value reached in one or more predetermined periods after the salvo of shots.

A fifth step consists of comparing the values of the measurements performed and acquired with theoretical values given by the heat equation adapted to the block of material under test, these theoretical values being obtained using a numerical modeling process, and of matching up these two series of values by varying one or more physical parameters of the material, such as the thickness of the superficial layer, the thermal conductivity of the superficial layer, the absorption coefficient of the superficial layer and/or the density of the superficial layer.

The numerical modeling can be obtained, as indicated above, using calculation software that is available on the market, such as the aforementioned MATLAB® or any similar software.

Preferably, the theoretical calculation of the heating takes into account the effects of the roughness of the surface of the material, nonhomogeneous heating of the material (for example, either due to an intrinsic nonhomogeneity of the material or due to a nonhomogeneity of the intensity of the laser beam), interference with the beam in the superficial layer, the thickness at which the temperature is measured, etc.

In light of the description given above, it is easy to see that the invention achieves the objects set forth.

It offers a number of advantages, particularly in that it makes it possible both to obtain a very good "signal-to-noise" ratio and to heat the material to a sufficient depth for the entire thickness of the thin superficial layer and/or the thermal contact between two layers to actually be involved.

It is not, however, limited to the exemplary embodiments explicitly described, particularly in reference to FIGS. 1 through 3.

Likewise, precise numerical examples have been given only in order to better demonstrate the essential features of the invention and are merely the result of a technological choice that is intrinsically within the capability of the Person Skilled The invention claied is:

1. A method for characterizing a block of material using active pyrometry, said block of material comprising at least two superposed layers, a superficial layer of small thickness disposed on a thick substrate, said superficial layer being brought to a predetermined initial temperature, the method comprising the steps of:

heating at least one predetermined area of a surface of said superficial layer of said block of material using a salvo of laser pulses and selecting said laser pulses with sufficiently high repetition frequency and sufficiently short duration so that said superficial layer of said block of material undergoes a plurality of thermal cycles consisting of a rapid temperature increase when the surface of said superficial layer is exposed to said laser pulses followed by a slow temperature decrease between two laser pulses in which the surface of said superficial layer is not allowed to return to said predetermined initial temperature, and for the surface of said superficial layer to accumulate heat from one thermal cycle to the next;

collecting all or part of thermal radiation emitted by the surface of said superficial layer of said block of material;

measuring at least part of said thermal radiation collected using a sensor;

determining temperature of the surface of said superficial layer from said thermal radiation measured by said sensor and processed by a signal acquisition and processing system;

analyzing predetermined heating and cooling time regimes by comparing measurements acquired by the signal acquisition and processing system with theoretical values given by a heat equation adapted to the physical characteristics of said block of material, and matching series of measured and theoretical values by varying at least one physical parameter associated with said block of material, so as to derive predetermined thermophysical properties of said block of material for characterizing said superficial layer.

2. The method of claim 1, further comprising the step of selecting thickness of said superficial layer to be between 0.1 μm and 900 μm.

3. The method of claim 1, further comprising the step of selecting said repetition frequency of said laser pulses to be between 1 kHz and 30 kHz.

4. The method of claim 1, further comprising the step of selecting said repetition frequency of said laser pulses to be 10 kHz and said duration to be equal to 90 ns.

5. The method of claim 1, further comprising the step of progressively increasing average temperature reached by said superficial layer with each of said plurality of thermal cycles as a result of temperature accumulation and wherein said salvo of laser pulses includes a sufficient number of successive pulses to obtain a saturation of said average temperature.

6. The method of claim 1, wherein the step of analyzing comprises the step of measuring and evaluating at least one of the following: average increase in temperature of said superficial layer, time evolution of the temperature during the heating in each thermal cycle or selectively for predetermined thermal cycles, the average maximum temperature value reached, the maximum temperature value reached for each thermal cycle or selectively for predetermined thermal cycles, the temperature value reached just before each laser pulse or selectively before predetermined laser pulses, the temperature value in one or more predefined time intervals between two laser pulses as compared to the previous laser pulse, the time evolution of the temperature between two laser pulses, the time evolution of the temperature after the end of said salvo of laser pulses, and the temperature value reached in one or more predetermined periods after said salvo of laser pulses.

7. The method of claim 1, wherein the step of analyzing comprises the step of obtaining variation of said at least one physical parameter of said superficial layer of said block of material by modifying at least one of the following: thickness of said superficial layer, thermal conductivity of said superficial layer, thermal resistance between two layers of said block of material, absorption coefficient of said superficial layer and density of said superficial layer.

8. The method of claim 1, further comprising the step of obtaining said theoretical values using a numerical modeling process.

9. The method of claim 8, further comprising the step of performing said numerical modeling a MATLAB® calculation software.

10. Apparatus for implementing the method for characterizing a block of material of claim 1, comprising:

at least one heat source comprising a laser that generates pulses of predetermined wavelength at said high repetition frequency;

an optical transmitting device for transmitting said laser pulses and heating said superficial layer by exposing all or part of the surface of said superficial layer;

an optical collecting device for collecting at least part of said thermal radiation emitted by the surface of said superficial layer of said block of material;

a sensor for measuring at least part of said thermal radiation collected and converting said thermal radiation measured into electrical signals; and a signal acquisition and processing device for receiving said electrical signals, determining evolution of the temperature, and comparing the evolution of temperature determined from measurement to the theoretical values so as to derive said predetermined thermophysical properties of said block of material for characterizing said superficial layer.

11. Apparatus of claim 10, wherein said laser is a diode-pumped "Nd:YAG" laser.

12. Apparatus of claim 11, wherein said laser is associated with a nonlinear potassium titanyl phosphate (KTP) crystal to double an emitted frequency of said laser pulses so that a wavelength of said laser pulses is equal to 532 nm.

13. Apparatus of claim 10, wherein said optical transmitting device further comprises a multimode optical fiber having an output coupled to an optical focusing element, which comprises at least one optical lens that projects said laser pulses onto the surface of said superficial layer of said block of material.

14. Apparatus of claim 13, wherein said optical focusing element is a galvanometric element, which is moved by a motor so as to scan a beam over the surface of said superficial layer.

15. Apparatus of claim 10, wherein said optical collecting device comprises an optical lens which receives all or part of the thermal radiation emitted by said superficial layer of said block of material, said optical lens is coupled with an optical fiber that conveys the thermal radiation collected to said sensor.

16. Apparatus of claim 10, wherein said sensor and said signal acquisition and processing system are constituted by a pyrometer equipped with a lens, which receives all or part of the thermal radiation emitted by said superficial layer of said block of material.

17. Apparatus of claim 16, wherein said pyrometer is a multi-channel pyrometer, thereby eliminating an emissivity specific to said block of material.

18. Apparatus of claim 10, wherein said signal acquisition and processing system is constituted by a computer system with a stored program, equipped with specific acquisition cards for receiving said electrical signals converted by said sensor.

19. Apparatus of claim 10, wherein said block of material moves relative to an assembly, constituted by said optical focusing element and said optical collecting device, to perform a mapping of thermophysical properties of said superficial layer.

* * * * *